(12) United States Patent
Nishi et al.

(10) Patent No.: US 10,799,010 B2
(45) Date of Patent: Oct. 13, 2020

(54) MAKEUP APPLICATION ASSIST DEVICE AND MAKEUP APPLICATION ASSIST METHOD

(71) Applicant: Panasonic Intellectual Property Management Co., Ltd., Osaka (JP)

(72) Inventors: Chie Nishi, Kanagawa (JP); Rieko Asai, Osaka (JP); Sachiko Takeshita, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 115 days.

(21) Appl. No.: 16/209,075

(22) Filed: Dec. 4, 2018

(65) Prior Publication Data

US 2019/0104827 A1 Apr. 11, 2019

Related U.S. Application Data

(63) Continuation of application No. PCT/JP2017/020453, filed on Jun. 1, 2017.

(30) Foreign Application Priority Data

Jul. 14, 2016 (JP) ................................. 2016-139500

(51) Int. Cl.
  *A45D 44/00* (2006.01)
  *G06T 7/00* (2017.01)
  (Continued)

(52) U.S. Cl.
  CPC ....... *A45D 44/005* (2013.01); *G06K 9/00221* (2013.01); *G06K 9/6212* (2013.01);
  (Continued)

(58) Field of Classification Search
  CPC .. A45D 44/005; A45D 2044/007; G06T 7/00; G06T 7/0012; G06T 7/60;
  (Continued)

(56) References Cited

U.S. PATENT DOCUMENTS

2016/0058158 A1* 3/2016 Tomita ............... H04N 5/23222
  348/78
2016/0196665 A1* 7/2016 Abreu ..................... G06T 7/251
  345/427

(Continued)

FOREIGN PATENT DOCUMENTS

| EP | 2953090 A1 | 12/2015 |
| JP | 57-072484 | 5/1982 |

OTHER PUBLICATIONS

International Search Report of PCT application No. PCT/JP2017/020453 dated Aug. 1, 2017.

(Continued)

*Primary Examiner* — Jon Chang
(74) *Attorney, Agent, or Firm* — Greenblum & Bernstein, P.L.C.

(57) ABSTRACT

A makeup application assist device includes an image acquisition circuitry which, in operation, acquires a user face image, a target face image, and an adjusted face image, an image determination circuitry which, in operation, adopts a makeup item assigned to each of face parts in the target face image if a difference value between a facial feature extracted from the user face image and a facial feature extracted from the target face image is less than or equal to a threshold value and adopts a makeup item assigned in the adjusted face image for each on a subset of the face parts having the feature that differs from the feature in the target face image if the difference value is greater than the threshold value, and an information generation circuitry which, in operation, generates makeup procedure information to be presented to (Continued)

a user, where the makeup procedure information includes a procedure for using the adopted makeup items.

9 Claims, 10 Drawing Sheets

(51) Int. Cl.
  *G06K 9/62* (2006.01)
  *G06K 9/00* (2006.01)
  *G16H 20/70* (2018.01)
  *G06T 7/60* (2017.01)
(52) U.S. Cl.
  CPC .............. *G06T 7/00* (2013.01); *G06T 7/0012* (2013.01); *G06T 7/60* (2013.01); *G16H 20/70* (2018.01); *A45D 2044/007* (2013.01); *G06T 2207/30201* (2013.01)

(58) Field of Classification Search
  CPC ........ G06T 2207/30201; G06K 9/6212; G06K 9/00221; G16H 20/70
  See application file for complete search history.

(56) References Cited

U.S. PATENT DOCUMENTS

2016/0357578 A1* 12/2016 Kim ..................... A45D 44/005
2017/0255478 A1* 9/2017 Chou ..................... G06F 3/012

OTHER PUBLICATIONS

The Extended European Search Report dated Jun. 25, 2019 for the related European Patent Application No. 17827269.6.

* cited by examiner

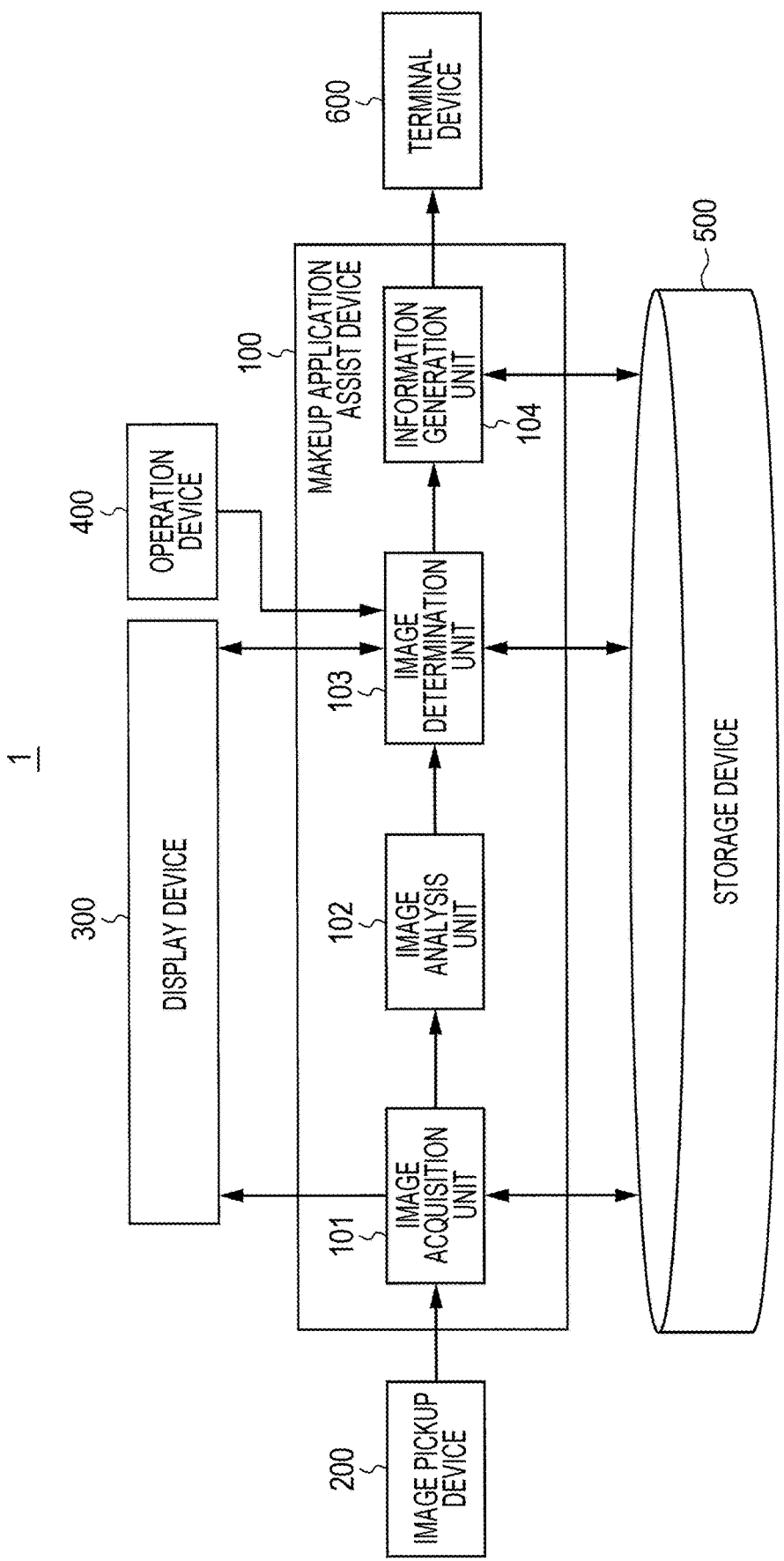

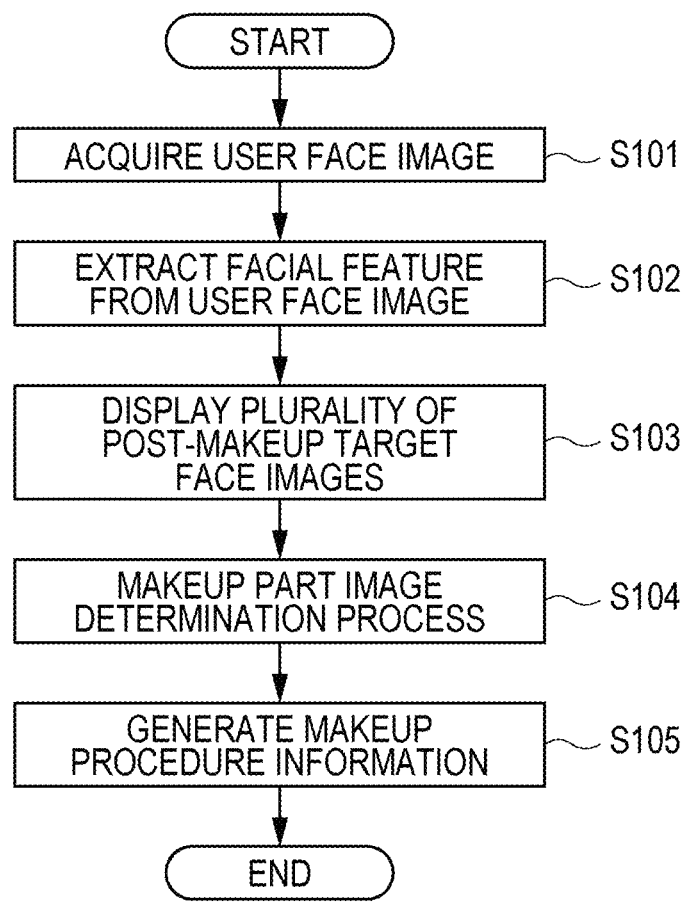

FIG. 3

| FACE PART | | TEMPLATE DATA SET | FIRST ADJUSTED DATA SET | SECOND ADJUSTED DATA SET | THIRD ADJUSTED DATA SET |
|---|---|---|---|---|---|
| FACE IMAGE | | 10 | 20 (j=1) | 30 (j=2) | 40 (j=3) |
| EYEBROW | EYEBROW (i=1) | 11 | 11 | 31 | 11 |
| EYESHADOW | EYE (EYELID) (i=2) | 12 | 12 | 12 | 12 |
| EYE LINER | EYE (LASH LINE) (i=3) | 13 | 23 | 13 | 43 |
| MASCARA | EYE (LASHES) (i=4) | 14 | 14 | 34 | 14 |
| BLUSH | CHEEK (CHEEK PORTION OF OUTLINE) (i=5) | 15 | 15 | 15 | 45 |
| FACIAL FEATURE INFORMATION (SHAPES OF FACE PARTS) | | OUTLINE: SHARP EYE: DOUBLE EYELID MOUTH: THIN LIPS | OUTLINE: SHARP EYE: MONOLID WIDE-SET EYES MOUTH: FULL LIPS | OUTLINE: OVAL EYE: DOUBLE EYELID, LARGE MOUTH: HEAVY LOWER LIPS | OUTLINE: ROUND EYE: DOUBLE EYELID MOUTH: THIN LIPS |
| FACIAL FEATURE INFORMATION (SKIN COLOR - HAIR COLOR) | | YELLOW COLOR CATEGORY BLACK HAIR | WHITE COLOR CATEGORY BROWN HAIR | YELLOW COLOR CATEGORY BLACK HAIR | BROWN COLOR CATEGORY GREY HAIR |

FIG. 6

| | | | |
|---|---|---|---|
| | STEP 1. EYEBROW<br><br>Fill in the eyebrow using an eyebrow pencil from the middle to the outside end of the eyebrow and, subsequently, from the inside end to the middle of the eyebrow. | MODEL NUMBER: EB-001<br><br>PRODUCT FEATURES: Natural color, rub-off resistant, long wearing | TIPS<br><br>Fill in hairs one by one lightly in the direction of growth of the original hairs. |
| | STEP 2. EYESHADOW<br><br>Apply a thin line of eyeshadow (color) along the upper lash line with an eyeshadow brush and then blend the shade into your eyehole lightly. | MODEL NUMBER: ES-003<br><br>PRODUCT FEATURES: Easy to blur, no uneven coloring | TIPS<br><br>Relatively large brush facilitates blurring a wide area of the upper eyelid. |
| | STEP 3. BLUSH<br><br>Draw small circles around your cheekbone with a blush brash so as to blend the blush in an oval shape toward the outside of your face. | MODEL NUMBER: CK-005<br><br>PRODUCT FEATURES: Easily brought into tight contact with the skin, long wearing | TIPS<br><br>Use a round brush with many stiff but not too stiff bristles to get a natural look. |
| | STEP 4. LIPSTICK<br><br>Apply lipstick from the outside to inside of your top lip and then apply a lipstick from the outside to inside of your bottom lip. | MODEL NUMBER: RP-004<br><br>PRODUCT FEATURES: Translucent warm sense of color lipstick | TIPS<br><br>If you want matte finishing, don't use a brush. Pat gently onto the lips with a finger. |

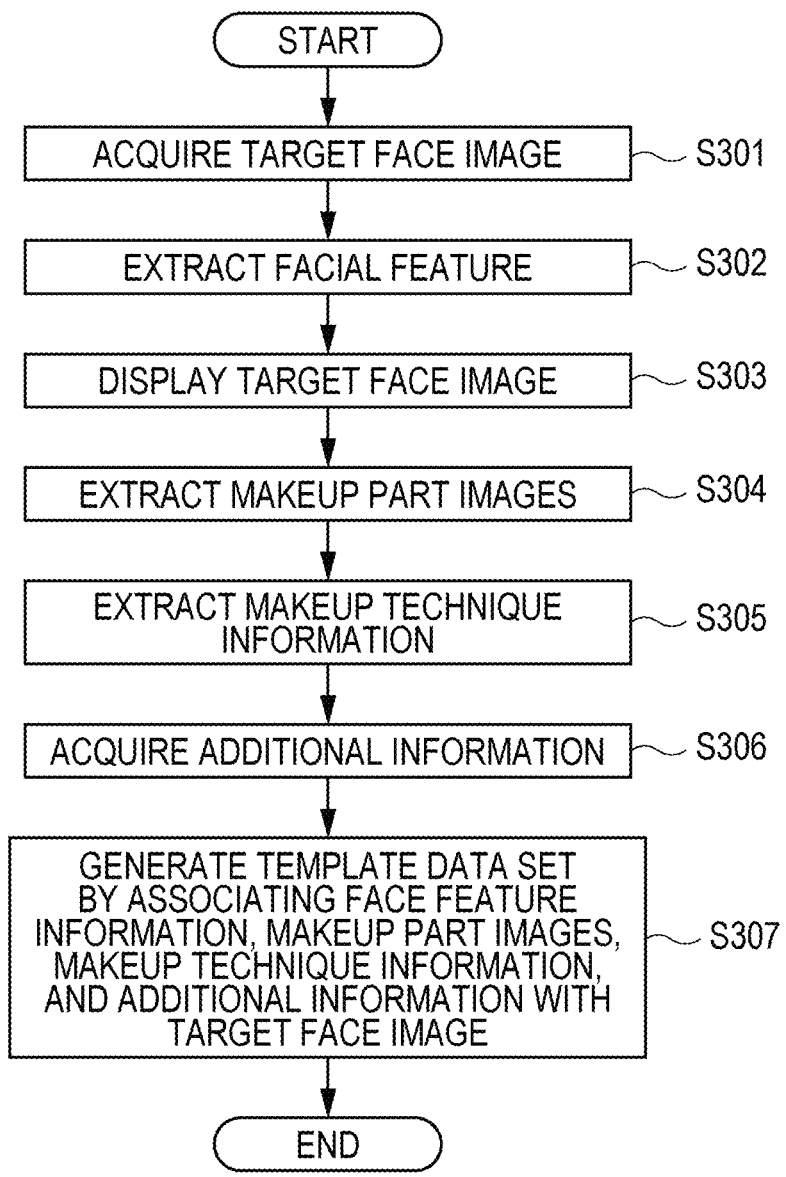

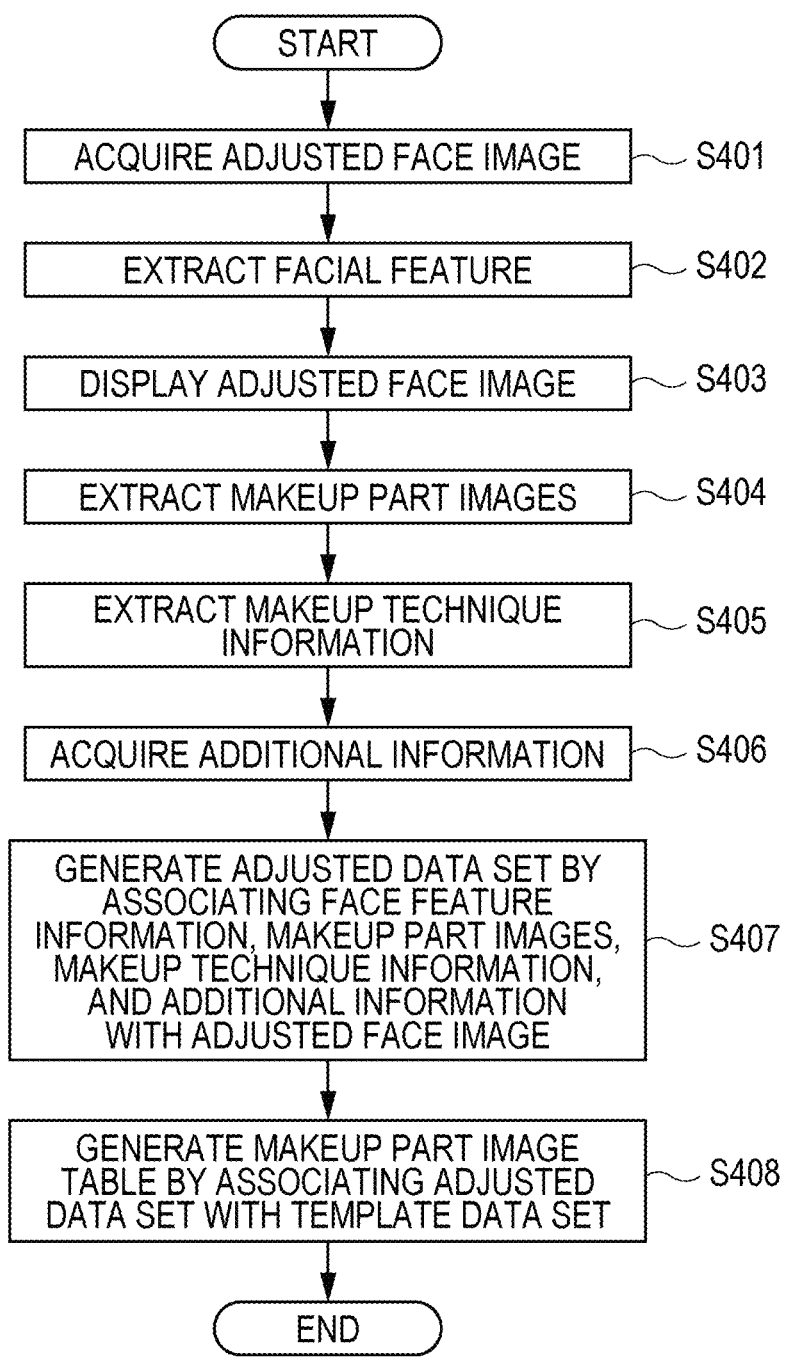

MAKEUP APPLICATION ASSIST DEVICE AND MAKEUP APPLICATION ASSIST METHOD

BACKGROUND

1. Technical Field

The present disclosure relates to a makeup application assist device and a makeup application assist method that assists a user in applying makeup.

2. Description of the Related Art

For example, after a user goes to a makeup salesperson at an in-store makeup counter to have makeup applied to their face, the user may attempt to apply that makeup to their face again by themselves. However, it may be difficult for the user to apply makeup to the user's face in the same manner as the makeup salesperson. In addition, for example, even when the user visits the in-store makeup counter again, another makeup salesperson may apply makeup on the user. Thus, the user may not get the same makeup as before.

To solve the above problem, a technique has been developed that generates a simulation image by superimposing an image indicating finished makeup on the face image (refer to, for example, Japanese Patent No. 1715357). Examples of an image superimposed on the face image (hereinafter referred to as a "makeup part image") include an image representing a makeup item, such as an eyeshadow or a blush.

For example, a shop terminal provided at an in-store makeup counter generates a simulation image indicating a makeup recommended by a makeup salesperson and transmits the simulation image to a user terminal, such as a smartphone. As a result, the user can apply makeup on their face by themselves while viewing the simulation image displayed on the user terminal, so that the reproducibility of the makeup improves. In addition, since simulation images are stored in the shop terminal, and the stored images are shared among a plurality of makeup salespersons, the reproducibility of the makeup is improved even when the user revisits the in-store makeup counter to have makeup applied.

SUMMARY

A makeup part image is generated by drawing or painting one of various makeup items (e.g., eyebrow, eyelid, blush, and lips) on the corresponding one of face parts in the face image of a model. At this time, it rarely happens that the features of all face parts of the user are the same as those of the face of the model. If a makeup part image corresponding to a face part having different feature is selected, the makeup part image is deformed and displayed so as to match the feature of the face part of the user. As a result, a simulation image may be obtained indicating an unnatural makeup that does not maintain the balance of each part of the face.

One non-limiting and exemplary embodiment provides a makeup application assist device capable of providing a user with a natural makeup that maintains the balance of each part of the face.

In one general aspect, the techniques disclosed here feature a makeup application assist device including an image acquisition circuitry which, in operation, acquires a user face image, a target face image in which a makeup item having predetermined shape and color is assigned to each of face parts, and an adjusted face image in which a feature of each on a subset of the face parts differs from a feature of the face part in the target face image and a makeup item having predetermined shape and color is assigned to each of the face parts, an image determination circuitry which, in operation, adopts the makeup item assigned to a face part in the target face image if a difference value between a facial feature extracted from the user face image and a facial feature extracted from the target face image is less than or equal to a threshold value and adopts the makeup item assigned to each on the subset of the face parts in the adjusted face image and the makeup item assigned to each of the rest of the face parts in the target face image if the difference value is greater than the threshold value, and an information generation circuitry which, in operation, generates makeup procedure information to be presented to a user, where the makeup procedure information includes a procedure for using the adopted makeup items.

According to the present disclosure, a natural makeup that maintains the balance of each part of the face can be provided to a user.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 is a block diagram illustrating an example of the configuration of a makeup application assist system and a makeup application assist device according to the present disclosure;

FIG. 2 is a flowchart illustrating an example of the overall operation performed by the makeup application assist device according to the present disclosure;

FIG. 3 is a diagram illustrating an example of a makeup part image table according to the present disclosure;

FIG. 6 is a diagram illustrating an example of displayed makeup procedure information according to the present disclosure;

FIG. 7 is a flowchart illustrating an example of the flow of a template data set generation process according to the present disclosure;

FIG. 8 is a flowchart illustrating an example of the flow of an adjusted data set generation process according to the present disclosure;

DETAILED DESCRIPTION

Figure 4:
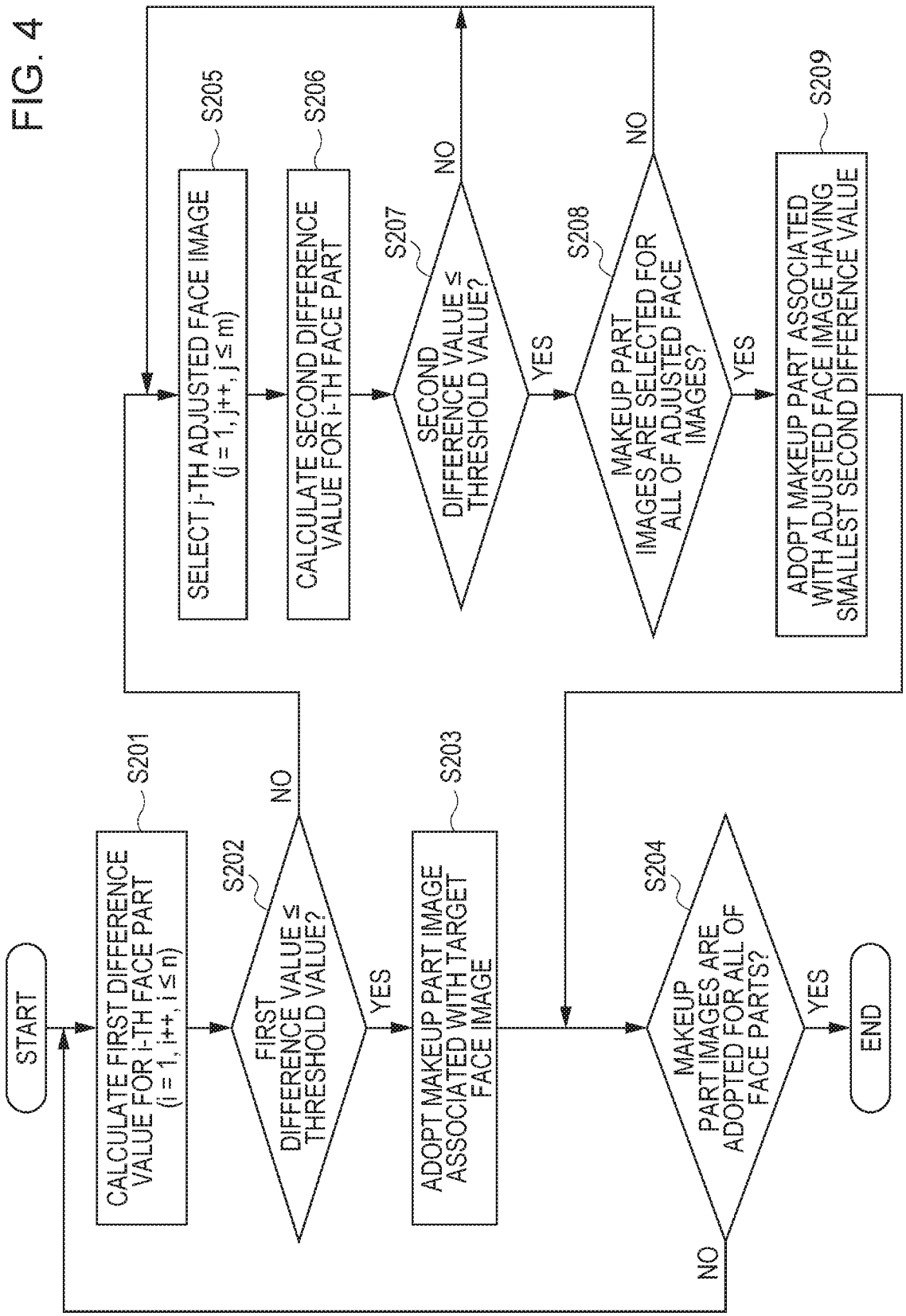
FIG. 4 is a flowchart illustrating an example of the flow of a makeup part image determination process performed by the makeup application assist device according to the present disclosure.

An embodiment of the present disclosure is described in detail below with reference to the accompanying drawings.

Underlying Knowledge Forming Basis of the Present Disclosure

For example, a makeup part image used in a makeup simulation system is a generated by a professional makeup artist or the like who draws or paints one of various makeup items (e.g., eyebrow, eyeshadow, blush, lipstick) on corresponding one of the face parts (e.g., eyebrows, eyelids, cheeks, and lips) in the face image of a model. In the makeup simulation system, the makeup part image generated in this manner can be selected and can be displayed and superimposed on the face image of a user by a user or a salesperson at an in-store makeup counter.

At this time, it rarely happens that the features of all face parts of the user are the same as those of the face of the model. If the feature of a face part corresponding to the selected makeup part image differs from the feature of the face part of the user, the makeup simulation system deforms the selected makeup part image in accordance with the feature of the user's face part and displays the makeup part image. As a result, a simulation image is displayed that indicates an unnatural makeup that does not maintain the balance of each part of the face.

Accordingly, the present disclosure provides a user with a natural makeup that maintains the balance of each part of the face.

System Configuration

First, the configuration of a makeup application assist system including a makeup application assist device according to the present embodiment is described first with reference to FIG. 1.

FIG. 1 is a block diagram illustrating an example of a makeup application assist system and a makeup application assist device.

A makeup application assist system 1 illustrated in FIG. 1 is disposed in, for example, a factory, a cosmetics selling store, a beauty salon, a medical institution, a makeup room for personal grooming, an event site, a private residence, or the like.

As illustrated in FIG. 1, the makeup application assist system 1 includes a makeup application assist device 100, an image pickup device 200, a display device 300, an operation device 400, a storage device 500, and a terminal device 600.

The makeup application assist device 100 is a device that assists a user in applying makeup. The makeup application assist device 100 is disposed in, for example, a factory, a cosmetics selling store, a beauty salon, a medical institution, a makeup for personal grooming, an event site, a private residence, and the like. The makeup application assist device 100 may be a stationary device or a portable device which may be easily carried. The configuration of the makeup application assist device 100 is described below.

The image pickup device 200 captures the frontal face image of the user. At this time, for example, the image of the face with no makeup is captured. Hereinafter, a still image obtained by capturing the frontal image of the user's face without makeup is referred to as a "user face image".

The image pickup device 200 outputs the user face image to the makeup application assist device 100.

The display device 300 displays, for example, the user face image having a makeup part image superimposed thereon or a target face image having a makeup part image superimposed thereon.

The makeup part image is an image representing the shape and color of a makeup item. Examples of a makeup item include eyebrow, eyeshadow, eye liner, mascara, blush, and lipstick.

The target face image is a still image obtained by capturing the frontal face image of a model wearing no makeup and being selected by the user as a model with a face the user wants to have. The model is not limited to a professional model, but may be an ordinary person, for example. A plurality of still images obtained by capturing the frontal face images of a plurality of models may be stored in advance in the storage device 500 as target face images. In addition, a still image serving as a target face image may be acquired via the image pickup device 200 or a network and be stored in the storage device 500.

Hereinafter, the user face image having a makeup part image superimposed thereon is referred to as a "post-makeup user face image", and the target face image having a makeup part image superimposed thereon is referred to as "post-makeup target face image". Note that the post-makeup user face image may be also referred to as a "simulation image".

The operation device 400 receives various kinds of operations performed by the user (for example, an operation to select a post-makeup target face image, which is described below). Thereafter, the operation device 400 notifies the makeup application assist device 100 of the information about the operation.

The storage device 500 is provided in, for example, a server apparatus (not illustrated) on the network. The storage device 500 stores a variety of types of information. For example, the storage device 500 stores a makeup part image table (described in more detail below, refer to FIG. 3). In addition, for example, the storage device 500 stores makeup procedure information (described in more detail below) for each of users (for each piece of user identification information). Furthermore, the storage device 500 stores a plurality of target face images and a plurality of post-makeup target face images. The post-makeup target face images may be stored in advance in the storage device 500 or may be acquired via a network and be stored in the storage device 500.

The terminal device 600 is used by, for example, a user. An example of the terminal device 600 is a smartphone or a tablet. The terminal device 600 can communicate with the makeup application assist device 100.

Note that at least one of the image pickup device 200, the display device 300, the operation device 400, and the storage device 500 may be included in the makeup application assist device 100.

Configuration of Device

The configuration of the makeup application assist device 100 is described below with reference to FIG. 1.

As illustrated in FIG. 1, the makeup application assist device 100 includes an image acquisition unit 101, an image analysis unit 102, an image determination unit 103, and an information generation unit 104.

Although not illustrated, the makeup application assist device 100 includes a central processing unit (CPU), a storage medium, such as a read only memory (ROM), that stores a control program, a working memory, such as a random access memory (RAM), and a communication circuit. In this case, the function of each of the units illustrated in FIG. 1 is provided by the CPU executing the control program.

The image acquisition unit 101 acquires a user face image from the image pickup device 200, stores the user face image in the storage device 500, and outputs the user face image to the image analysis unit 102. The user face image stored in the storage device 500 is associated with the user identification information.

Upon receiving the user face image from the image acquisition unit 101, the image analysis unit 102 extracts the facial feature from the user face image. For example, the image analysis unit 102 extracts a plurality of facial feature points (refer to FIGS. 5, 9, and 10) and extracts the shape and position of each of the face parts (for example, the eyes, eyelids, cheeks, nose, lips, forehead, and chin) on the basis of the facial feature points. In addition, the image analysis unit 102 extracts, for example, the colors of the hair, skin, pupil, and lip of the user.

As a facial feature point extraction method and a face part extraction method, widely used classification methods, pattern recognition methods, clustering methods, and optimization methods can be employed. Examples of a widely used classification method include decision tree analysis, neural networks (including deep learning), and naive Bayes. Examples of a widely used pattern recognition method include neural networks (including deep learning) and support vector machines (SVMs). Examples of a widely used clustering method include k-Nearest Neighbor (k-NN) method, k-means, and hierarchical clustering. In addition, an example of a widely used optimization method is a genetic algorithm.

The image analysis unit 102 outputs, to the image determination unit 103, the facial feature information indicating the extracted facial feature. For example, the facial feature information includes the information about the shape and position (the facial feature point) of each of the extracted face parts and the colors (RGB, luminance) of the hair, skin, pupil, and lip.

Upon receiving the facial feature information from the image analysis unit 102, the image determination unit 103 stores, in the storage device 500, the facial feature information in association with the user identification information.

Thereafter, the image determination unit 103 acquires a plurality of post-makeup target face images from the storage device 500 and displays the post-makeup target face images by using the display device 300. The processes performed by the image determination unit 103 are described in detail below with reference to FIG. 4 and other figures.

At this time, the user performs an operation to select, from among the plurality of post-makeup target face images displayed as options, the desired one (an operation to select a post-makeup target face image). For example, the user selects a post-makeup target face image that matches the makeup look that the user desires. Note that each of the post-makeup target face images displayed as options may be an image obtained by superimposing a makeup part image on the face image of a model or the image of a photo of the face of the model who actually wears makeup. Note that the user can manually select, from a list of the post-makeup target face images, the one close to the face they want to have. Alternatively, the user may be allowed to select a keyword representing the face they want to have, such as "double eyelid", "long face", or "sharp face line" and, thereafter, select, from among the target face images and adjusted face images (described below) in the makeup part image table, the one the closest to the face they want to have.

When the operation device 400 receives the operation performed by the user to select the post-makeup target face image, the image determination unit 103 performs a makeup part image determination process. The makeup part image determination process is a process of determining makeup part images (makeup items) to be presented to the user on the basis of the post-makeup target face image selected by the user and at least one adjusted face image (described in more detail below) associated with the selected post-makeup target face image selected by the user. The makeup part image determination process is described below with reference to FIGS. 3 and 4.

Thereafter, the image determination unit 103 outputs, to the information generation unit 104, determination result information including the makeup part images determined in the makeup part image determination process, the names of the makeup items each corresponding to one of the makeup part images (hereinafter referred to as "item name information"), and information about how to use each of the makeup items (for example, the order in which the makeup items are used and a technique of applying each of the makeup items to the skin). Hereinafter, the information about how to use the makeup items is referred to as "makeup technique information").

The makeup technique information may include, for example, information about an amount of pressure applied to a brush, information about a makeup applying direction, information about a degree of blurring, and information indicating a comment of a creator of a makeup part image (a painter who painted the makeup item).

Upon receiving the determination result information from the image determination unit 103, the information generation unit 104 generates makeup procedure information on the basis of the determination result information and the user face image acquired from the storage device 500 and outputs the makeup procedure information to the terminal device 600. The makeup procedure information includes information to be presented to the user, such as the procedure for using the makeup items indicated by the makeup part images. The makeup procedure information is described in more detail below.

Operation Performed by Device

The overall operation performed by the makeup application assist device 100 (the operation to generate the makeup procedure information) is described below with reference to FIG. 2.

FIG. 2 is a flowchart illustrating an example of the overall operation performed by the makeup application assist device 100.

In step S101, the image acquisition unit 101 acquires the user face image from the image pickup device 200. Thereafter, the image acquisition unit 101 outputs the user face image to the image analysis unit 102. In addition, the image acquisition unit 101 stores, in the storage device 500, the user face image in association with user identification information.

In step S102, the image analysis unit 102 extracts the facial feature from the user face image received from the image acquisition unit 101. Thereafter, the image analysis unit 102 outputs, to the image determination unit 103, the facial feature information indicating the extracted facial feature.

In step S103, the image determination unit 103 acquires a plurality of post-makeup target face images from the storage device 500 and instructs the display device 300 to display the post-makeup target face images as options. The process performed by the image determination unit 103 is described in detail below with reference to FIG. 4 and other figures.

In step S104, when the operation device 400 receives the operation performed by the user to select the post-makeup target face image, the image determination unit 103 performs the makeup part image determination process described below. Thereafter, the image determination unit 103 outputs, to the information generation unit 104, the determination result information including the makeup part images, the item name information, and the makeup technique information determined in the makeup part image determination process.

In step S105, the information generation unit 104 generates makeup procedure information on the basis of the user face image acquired from the storage device 500 and the determination result information received from the image determination unit 103. Thereafter, the information generation unit 104 outputs the makeup procedure information to the terminal device 600.

An example of the overall operation performed by the makeup application assist device 100 has been described so far.

An example of the makeup part image determination process performed by the makeup application assist device 100 (step S104 illustrated in FIG. 2) is described below with reference to FIGS. 3 and 4.

FIG. 3 is a diagram illustrating an example of a makeup part image table used in the makeup part image determination process. FIG. 4 is a flowchart illustrating an example of the flow of the makeup part image determination process performed by the makeup application assist device 100.

The makeup part image table is described first with reference to FIG. 3.

As illustrated in FIG. 3, the makeup part image table includes a plurality of adjusted data sets (three adjusted data sets in the example in FIG. 3) registered in association with one template data set.

The template data set includes, for example, a target face image 10, makeup part images 11 to 15, and the facial feature information.

The target face image 10 is a frontal face image (a still image) of a model without makeup. The target face image 10 is superimposed with the makeup part images 11 to 15 to form a post-makeup target face image. As described above, the formed post-makeup target face image is displayed on the display device 300 as an option.

The makeup part image 11 is an image representing the shape and color of eyebrow makeup (an example of a makeup item) applied to the eyebrow (an example of a face part).

The makeup part image 12 is an image representing the shape and color of an eyeshadow (an example of a makeup item) applied to the eye (an example of a face part).

The makeup part image 13 is an image representing the shape and color of an eye line (an example of a makeup item) applied to the eye (an example of a face part).

The makeup part image 14 is an image representing the shape and color of a mascara (an example of a makeup item) applied to the eye (an example of a face part).

The makeup part image 15 is an image representing the shape and color of blush (an example of a makeup item) applied to the cheek (an example of a face part).

In this example, each of the makeup part images 11 to 15 represents the shape and color of the makeup item. However, each of the makeup part images 11 to 15 may represent only the shape, and information about the color for each of the makeup part images 11 to 15 may be separately registered.

The facial feature information is information about the facial feature extracted from the target face image 10. In the example illustrated in FIG. 3, the shapes of the face parts (for example, the outline, eyes, and mouth), the skin color, and the hair color are illustrated. However, facial feature information is not limited thereto. The facial feature information may further include the positions of the face parts and the lip color. In addition, in the example illustrated in FIG. 3, for simplicity of description, the facial feature information is described by using text. However, the values representing the facial feature (for example, the coordinates of facial feature points, RGB values, and brightness values) may be registered. Note that the term "outline" refers to the shape of the outer periphery of the face excluding the hair portion. The outline is defined as one of the face parts and constitutes the face together with the other face parts, such as the eyes, nose, mouth, and cheeks.

Although not illustrated, the template data set includes makeup technique information in addition to the information illustrated in FIG. 3. As described above, the makeup technique information is information indicating how to use the makeup items (for example, the order in which the makeup items are used and the technique for applying the makeup items to the skin). The template data set may further include, for example, additional input information regarding the makeup items (described in more detail below).

A template data set generation process is described below with reference to FIG. 7.

Like the template data set, each of the adjusted data sets also includes a face image (hereinafter referred to as an "adjusted face image"), a variety of makeup part images, and a variety of pieces of facial feature information. The adjusted face image is an image obtained by capturing the frontal face image (a face image without makeup) of a model in which a feature of each on a subset of the face parts differs from a feature of the face part in the target face image.

For example, in first adjusted data set, an adjusted face image 20 is registered as a face image in which the shape of the eye (the shape of the lash line) differs from that in the target face image 10. In addition, in the first adjusted data set, as the eye-line makeup part image corresponding to the eye (the lash line), a makeup part image 23 is registered. The makeup part image 23 has a shape that differs from the makeup part image 13 of the template data set.

In addition, for example, in a second adjusted data set, an adjusted face image 30 is registered as a face image in which the shapes of eyebrow and eye (lashes) differ from those of the target face image 10. In addition, in the second adjusted data set, as the eyebrow makeup part image corresponding to the eyebrow, a makeup part image 31 having a different shape from the makeup part image 11 of the template data set is registered. Furthermore, in the second adjusted data set, as a mascara makeup part image corresponding to the eyes (lashes), a makeup part image 34 having a shape that differs from the makeup part image 14 of the template data set is registered.

In addition, for example, in third adjusted data set, an adjusted face image 40 is registered as a face image in which the shapes of eye (the lash line) and cheek (the cheek portion of the outline) differ from those of the target face image 10. In addition, in the third adjusted data set, as the eye-line makeup part image corresponding to the eye (the lash line), a makeup part image 43 having a shape that differs from the makeup part image 13 of the template data set is registered. Furthermore, in the third adjusted data set, as a blush makeup part image corresponding to the cheek (the cheek portion of the outline), a makeup part image 45 having a shape that differs from the makeup part image 15 of the template data set is registered.

Although not illustrated, like the template data set, each of the adjusted data sets includes makeup technique information. In addition, each of the adjusted data sets may include additional information and the like (described in more detail below).

In addition, in the example illustrated in FIG. 3, three adjusted data sets are provided. However, the number of adjusted data sets is not limited thereto. Note that to determine makeup part images suitable for the user's facial feature, it is desirable that a large number of adjusted data sets be provided.

An adjusted data set generation process is described below with reference to FIG. 8.

For example, the makeup part image table described above is generated for each of the target face images (for each of the template data sets). Accordingly, the number of makeup part image tables to be generated is determined by the number of the post-makeup target face images to be presented to the user as options.

The makeup part image table has been described so far.

The flow of the makeup part image determination process is described below with reference to FIG. 4. In the makeup part image determination process, for each of the types of makeup part images (the makeup items) registered in the makeup part image table, a makeup part image registered in either the template data set or the adjusted data set is determined.

In step S201, the image determination unit 103 calculates a first difference value for the i-th face part.

Here, i represents the number of types of face parts registered in the makeup part image table. In the case of the makeup part image table illustrated in FIG. 3, five types of face parts, that is, the eyebrow (i=1), the eyelid (i=2), the lash line (i=3), the eyelashes (i=4), and cheek (i=5) are registered.

The term "first difference value" refers to a value indicating the difference between the feature relating to the i-th face part extracted from the user face image and the feature relating to the i-th face part extracted from the target face image. For example, when the face part is an eye (for example, when determining an eyeshadow image, an eye line image, and a mascara image), a process to compare the eye shape in the user face image with the eye shape in the target face image is performed. A specific example of the process is described below with reference to FIG. 5.

Figure 5:
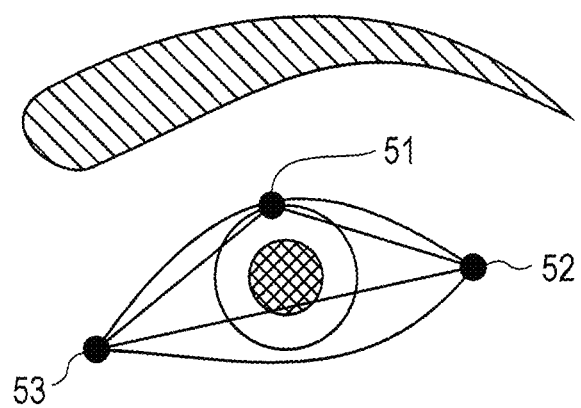
FIG. 5 is a diagram illustrating a particular example of a feature comparison process according to the present disclosure.

FIG. 5 illustrates an example of facial feature points around the left eye extracted from the user face image, for example. In FIG. 5, the image determination unit 103 calculates the degree of similarity of a triangle formed by three points, that is, an upper eyelid facial feature point 51, an eye outer corner facial feature point 52, and an eye inner corner facial feature point 53. Similarly, although not illustrated in the figure, the image determination unit 103 calculates the degree of similarity of a triangle formed by the three points, that is, an upper eyelid facial feature point, an eye outer corner facial feature point, and an eye inner corner facial feature point in the target face image. Thereafter, the image determination unit 103 calculates a difference between the two calculated degrees of similarity.

The method for calculating the first difference value by comparing the features is not limited to that described in FIG. 5. Other examples are described later.

In step S202, the image determination unit 103 determines whether the first difference value is less than or equal to a predetermined threshold value. The threshold value is, for example, an upper limit value up to which the features of two face parts to be compared are considered to be similar.

If the first difference value is greater than the threshold value (step S202: NO), the flow proceeds to step S205. Step S205 and the subsequent steps are described later.

If the first difference value is less than or equal to the threshold value (step S202: YES), the flow proceeds to step S203.

In step S203, the image determination unit 103 adopts a makeup part image associated with the target face image for the i-th face part. For example, in FIG. 3, when i=1 (when the face part is an eyebrow), the image determination unit 103 adopts the makeup part image 11 (an eyebrow image) associated with the target face image 10.

In step S204, the image determination unit 103 determines whether a makeup part image has been adopted for each of all the face parts.

If a makeup part image has been adopted for each of all the face parts (step S204: YES), the series of processes ends.

However, if a makeup part image has not been adopted for any one of the face parts, that is, if there is a remaining face part for which any makeup part image is not adopted (step S204: NO), the flow returns to step S201.

If in step S202, the first difference value is greater than the threshold value (step S202: NO), the feature of the i-th face part in the user face image and the feature of the i-th face part in the target face image are not similar. In this case, the image determination unit 103 selects, from one of the adjusted data sets associated with the template data set, the makeup part image corresponding to the i-th face part.

In step S205, the image determination unit 103 selects the j-th adjusted face image.

Here, j is the number of adjusted face images registered in the makeup part image table. In the case of the makeup part image table illustrated in FIG. 3, three adjusted face images 20, 30, and 40 are registered.

In step S206, the image determination unit 103 calculates a second difference value for the i-th face part. At this time, the image determination unit 103 temporarily stores the calculated second difference value.

The term "second difference value" refers to a value indicating the difference between the feature relating to the i-th face part extracted from the user face image and the feature relating to the i-th face part extracted from the j-th adjusted face image. For example, when the face part is an eye, the shape of the eye in the user face image is compared with the shape of the eye in the j-th adjusted face image. The description of the specific example is the same as the description given previously in FIG. 5. Accordingly, the description is not repeated.

In step S207, the image determination unit 103 determines whether the second difference value is less than or equal to a predetermined threshold value. For example, the threshold value is the same as the threshold value used in step S202.

If the second difference value is greater than the threshold value (step S207: NO), the flow proceeds to step S205.

If the second difference value is less than or equal to the threshold value (step S207: YES), the flow proceeds to step S208.

In step S208, the image determination unit 103 determines whether all the adjusted face images have been selected.

If all the adjusted face images have not been selected (step S208: NO), the flow proceeds to step S205.

If all the adjusted face images have been selected (step S208: YES), the flow proceeds to step S209.

In step S209, the image determination unit 103 adopts a makeup part image associated with the adjusted face image having the smallest second difference value for the i-th face part. For example, in FIG. 3, when i=3 (when the face part is the eye (the lash line)), the image determination unit 103 adopts, out of the makeup part image 23 and the makeup part image 43 (i.e., the eye line images), the one associated with the adjusted face image and having a smaller second difference value.

Note that if, in step S209, a plurality of second difference values are the smallest, one of the adjusted face images may be selected on the basis of a predetermined weight, and a makeup part image may be adopted from the adjusted face image. The example is described later.

After step S209, the flow proceeds to step S204.

As described above, after completion of the makeup part image determination process illustrated in FIG. 4, the image determination unit 103 outputs, to the information generation unit 104, the determination result information including the adopted makeup part images, the item name information, and the makeup technique information.

As described above, in the makeup part image determination process, if the feature of a predetermined face part in the user face image is similar to that in the target face image, the makeup part image associated with the target face image and corresponding to the face part is adopted. However, if the feature of the predetermined face part in the user face image is not similar to that in the target face image, the makeup part image associated with the adjusted face image and corresponding to the face part is adopted. As a result, a makeup part image that matches the feature of each of the face parts of the user is adopted and, thus, a natural makeup that maintains the balance of each part of the face can be presented to the user.

An example of the makeup part image determination process has been described so far.

An example of the makeup procedure information generated by the information generation unit 104 is described below.

The information generation unit 104 generates makeup procedure information on the basis of the user face image acquired from the storage device 500 and the determination result information received from the image determination unit 103. The determination result information includes at least the makeup part images determined in the makeup part image determination process, item name information indicating the names of makeup items each corresponding to one of the makeup part images, a technique of using the makeup items (for example, the order in which the makeup items are used, the technique of applying each of the makeup items to the skin, and the like).

For example, the information generation unit 104 generates screen information as an example of makeup technique information and outputs the screen information to the terminal device 600. The screen information is displayed on a display unit (not illustrated) of the terminal device 600.

An example of the screen information displayed by the terminal device 600 is described below. FIG. 6 is a diagram illustrating an example of the displayed screen information.

As illustrated in FIG. 6, for each of the makeup items, the screen information includes a makeup part image 71 superimposed on a user face image 70, item name information 72, and use order information 73 indicating the order in which the makeup items are used, and application technique information 74 indicating how to apply the makeup item to the skin. Although not illustrated, various types of information included in the makeup technique information may be displayed in a predetermined format. Examples of the various types of information include brush pressure, information indicating an application direction (a direction of moving a brush or the like), information indicating the degree of blurring, and information indicating the comment of a painter of the makeup item.

In addition, as illustrated in FIG. 6, product information 75 and advice information 76 may be displayed for each of the makeup items. The product information 75 is, for example, information indicating the model number of the makeup item and the characteristics of the makeup item. The advice information 76 is information indicating tips on how to use the makeup item. The product information 75 and the advice information 76 are examples of additional information and are input by, for example, a makeup salesperson at an in-store makeup counter. The product information 75 and the advice information 76 are registered in the makeup part image table, for example. In this case, the determination result information output to the information generation unit 104 includes the product information 75 and the advice information 76.

Although not illustrated in FIG. 6, the post-makeup user face image (the simulation image) may be displayed as a face sample wearing makeup. In the example illustrated in FIG. 6, the post-makeup user face image is generated by superimposing all the makeup part images (the eyebrow image, the eyeshadow image, the blush image, and the lipstick image) on the user face image 70.

Since as described above, the screen information includes detailed information, such as the order in which the makeup items are used and the technique for applying the makeup items, the user can reproduce the desired makeup look by applying makeup while referring to the screen information illustrated in FIG. 6 and displayed on the terminal device 600.

Note that in addition to the various types of information illustrated in FIG. 6, the makeup procedure information (for example, the screen information) may include, for example, information indicating the look after makeup, the user identification information, information enabling the user to identify the screen information, and information enabling the user to identify the makeup items.

An example of the makeup procedure information has been described so far.

An example of the template data set generation process is described below with reference to FIG. 7.

FIG. 7 is a flowchart illustrating the flow of the template data set generation process.

In step S301, the image acquisition unit 101 acquires, for example, a target face image captured by the image pickup device 200. Thereafter, the image acquisition unit 101 outputs the target face image to the image analysis unit 102.

In step S302, the image analysis unit 102 extracts the facial feature from the target face image. Thereafter, the image analysis unit 102 outputs facial feature information indicating the extracted facial feature and the target face image to the image determination unit 103.

In step S303, the image determination unit 103 causes the display device 300 to display the target face image received from the image analysis unit 102.

At this time, the creator of the makeup part image (the painter of the makeup item and, for example, a professional makeup artist) performs an operation of drawing or painting, on the displayed target face image, a variety of makeup items each having a predetermined shape and a predetermined color. In addition, the creator inputs the comment for the drawn or painted makeup item, as necessary.

The operation device 400 receives the above-described operation, and outputs, to the image determination unit 103, drawing information about the details of drawing and the comment. Examples of the details of drawing include the order in which the makeup items are drawn or painted, the shape and color of each of the makeup items, the degree of blurring of each of the makeup items, the position of each of the makeup items, the brush pressure applied when each of the makeup items is drawn or painted, and the application direction when each of the makeup items is drawn or painted.

In step S304, the image determination unit 103 extracts each of the makeup part images on the basis of the drawing information received from the operation device 400.

In step S305, the image determination unit 103 extracts the makeup technique information on the basis of the drawing information received from the operation device 400.

In addition, for example, after the various makeup items are drawn or painted by the creator, a makeup salesperson at an in-store makeup counter, for example, performs an operation to input additional information as necessary. An example of the additional information is the product information 75 and the advice information 76 illustrated in FIG. 6.

The operation device 400 receives the above-described operation and outputs the additional information to the image determination unit 103.

In step S306, the image determination unit 103 acquires the additional information from the operation device 400.

In step S307, the image determination unit 103 associates the facial feature information, the makeup part images, the makeup technique information, and the additional information with the target face image and generates a template data set. Thereafter, the image determination unit 103 stores the generated template data set in the storage device 500.

An example of the template data set generation process has been described so far.

An example of an adjusted data set generation process is described below with reference to FIG. 8.

FIG. 8 is a flowchart illustrating the flow of the adjusted data set generation process.

In step S401, the image acquisition unit 101 acquires, for example, an adjusted face image captured by the image pickup device 200. Thereafter, the image acquisition unit 101 outputs the adjusted face image to the image analysis unit 102.

As described above, the adjusted face image acquired here has a face image in which a feature of each on a subset of the face parts differs from a feature of the face part in the target face image. For example, from the image pickup device 200, the image acquisition unit 101 acquires, as an adjusted face image, a face image by capturing the face image of a model having the feature of a predetermined face part (e.g., the eyes) that differs from that in the target face image.

Note that as an adjusted face image, the image acquisition unit 101 may acquire, from among a plurality of face images prepared in the storage device 500 in advance, the one that meets a predetermined condition. An example of the process is described later.

In step S402, the image analysis unit 102 extracts the facial feature from the adjusted face image. Thereafter, the image analysis unit 102 outputs the facial feature information indicating the extracted facial feature and the adjusted face image to the image determination unit 103.

In step S403, the image determination unit 103 causes the display device 300 to display the adjusted face image received from the image analysis unit 102.

Here, the creator of the makeup part image (a person who drew or painted the makeup item and, for example, a professional makeup artist) performs an operation to draw or paint various makeup items each having a predetermined shape and a predetermined color on the displayed adjusted face image. In addition, the creator performs an operation to input the comment about each of the drawn or painted makeup items as necessary.

Note that in step S403, each of the makeup part images of the target face image may be superimposed on the adjusted face image and may be displayed. The makeup part images superimposed and displayed here correspond to the face parts each having a facial feature whose difference from that of the adjusted face image is less than or equal to the threshold value. Therefore, in the adjusted face image, the makeup part image is not displayed for a face part having the facial feature whose difference from that of the target face image is greater than the threshold value. In this case, the creator can draw or paint a makeup item for the face part for which a makeup part image is not displayed in the adjusted face image. Thus, the creator does not have to draw or paint all the makeup items, which saves the creator a lot of effort and time.

The operation device 400 receives the above-described operation and outputs, to the image determination unit 103, the drawing information indicating, for example, the drawn or painted image and the comment. Since the details of the drawing information is the same as that described for the template data set generation process, description of the details is not repeated.

Since the processing in steps S404 to S406 is the same as the processing in steps S304 to S306 illustrated in FIG. 7, description of the processing is not repeated.

In step S407, the image determination unit 103 generates an adjusted data set by associating the facial feature information, the makeup part images, the makeup technique information, and the additional information with the adjusted face image.

In step S408, the image determination unit 103 associates the generated adjusted data set with the template data set and generates a makeup part image table. Thereafter, the image determination unit 103 stores the makeup part image table in the storage device 500.

When a plurality of adjusted data sets are associated with the template data set, the flow illustrated in FIG. 8 can be repeated. In this manner, for example, the makeup part image table illustrated in FIG. 3 is generated.

An example of the adjusted data set generation process has been described so far.

Effect of Present Embodiment

As described above, according to the present embodiment, the makeup application assist device 100 includes the image acquisition unit 101, the image determination unit 103, and the information generation unit 104. The image acquisition unit acquires a user face image, a target face image in which a makeup item having predetermined shape and color is assigned to each of face parts, and an adjusted face image in which a feature of each on a subset of the face parts differs from a feature of the face part in the target face image and a makeup item having predetermined shape and color is assigned to each of the face parts. The image determination unit 103 adopts the makeup item assigned to a face part in the target face image if a difference value between a facial feature extracted from the user face image and a facial feature extracted from the target face image is less than or equal to a threshold value and adopts the makeup item assigned to each on the subset of the face parts in the adjusted face image and the makeup item assigned to each of the rest of the face parts in the target face image if the difference value is greater than the threshold value. The information generation unit 104 generates makeup procedure information to be presented to a user, where the makeup procedure information includes a procedure for using the adopted makeup items.

That is, according to the makeup application assist device 100 of the present embodiment, if the feature of a predetermined face part in the user face image is similar to that in the target face image, the makeup part image associated with the target face image is selected as the makeup part image corresponding to the face part. However, if the feature of the predetermined face part in the user face image is not similar to that in the target face image, the makeup part image associated with the adjusted face image is selected as the makeup part image corresponding to the face part. In this manner, the makeup part images that match the features of the face parts of the user are adopted. As a result, natural makeup that maintains the balance of each part of the face can be presented to the user.

Modification of Present Embodiment

While an embodiment of the present disclosure has been described above, the present disclosure is not limited to the above-described embodiment, and a variety of modifications can be made. The modifications are described below.

Modification 1

According to the above-described embodiment, as an example of the face part feature comparison process, the case in which the shapes of the eye are compared with each other has been described with reference to FIG. 5. However, the face part feature comparison process is not limited thereto.

Figure 9:
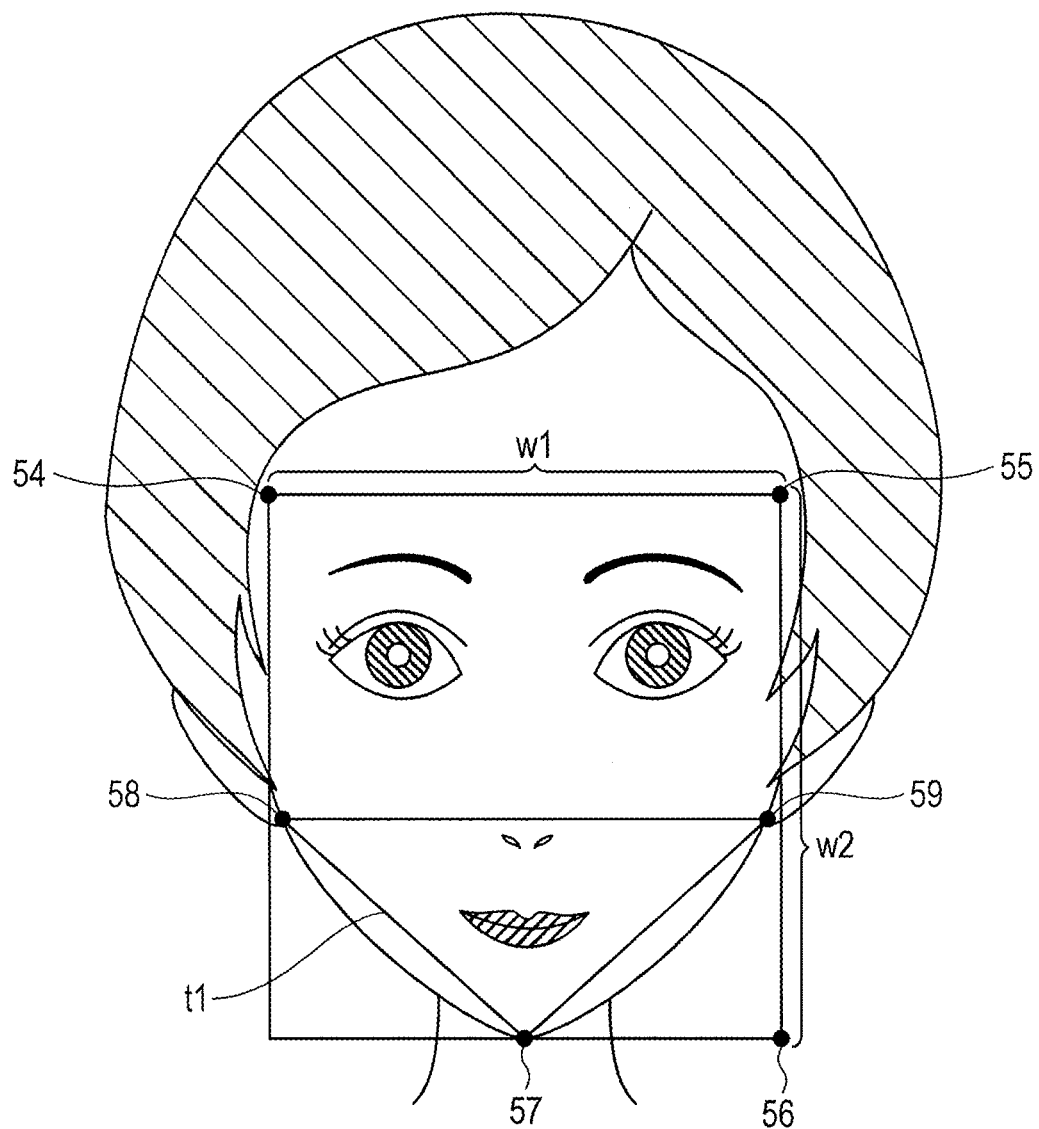
FIG. 9 is a diagram illustrating a particular example of a feature comparison process according to the present disclosure.

For example, the shapes of the outlines of the user face image and the target face image may be compared with each other. In this case, as illustrated in FIG. 9, the image determination unit 103 compares the following measures between the user face image and the target face image, that is, the width w1 of the face (the distance between a facial feature point 54 and a facial feature point 55), the length w2 of the face (the distance between the facial feature point 55 and a facial feature point 56), and the shape (the degree of similarity) of an inverted triangle t1 formed by a jaw facial feature point 57, a right cheek facial feature point 58, and a left cheek facial feature point 59. Thereafter, the image determination unit 103 computes the first difference value of each of the measures.

Subsequently, if the first difference value concerning each of the width w1 of the face, the length w2 of the face, and the inverted triangle t1 is less than or equal to a predetermined threshold value, the image determination unit 103 determines that the outline of the user face image is the same as (or similar to) that of the target face image. Thus, the image determination unit 103 adopts the makeup part images (for example, the images representing the makeup items corresponding to the outline, such as the blush, highlighting, and contouring) associated with the target face image.

Note that the process to compare the shapes of the outlines with each other can be applied not only to comparison of the user face image and the target face image but also to comparison of the user face image and an adjusted face image.

Modification 2

In the above-described embodiment and modification 1, as an example of a process to compare the features of face parts, the process to compare the face parts (the eyes or outlines) with each other has been described with reference to FIGS. 5 and 9. However, the comparison process is not limited thereto.

Figure 10:
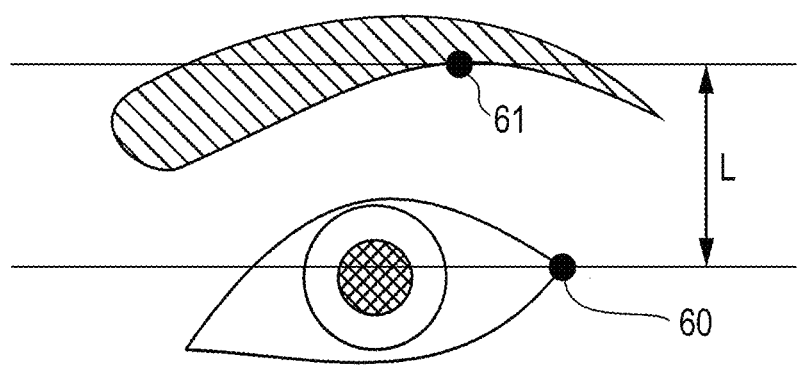
FIG. 10 is a diagram illustrating a particular example of a feature comparison process according to the present disclosure.

For example, the relative relationship between face parts in the user face image may be compared with the relative relationship between the face parts in the target face image. In this case, as illustrated in FIG. 10, the image determination unit 103 compares a distance L between an eye corner facial feature point 60 and an eyebrow arch peak facial feature point 61 (the vertical length of the eyelid) in the user face image with that in the target face image. Thus, the image determination unit 103 calculates the first difference value.

Thereafter, if the first difference value regarding the distance L is less than or equal to a predetermined threshold value, the image determination unit 103 determines that the eyes (eyelids) in the user face image are the same as (or similar to) those in the target face image. Thus, the image determination unit 103 adopts the makeup part image associated with the target face image (for example, the image representing the makeup item corresponding to the eyelid, such as eyeshadow).

Note that the process to compare the shapes of the outlines with each other can be applied not only to comparison of the user face image and the target face image but also to comparison of the user face image and an adjusted face image.

While the above description has been given with reference to the distance between two face parts (the eyebrow and the eye) as an example of the relative relationship between the face parts, the relative relationship is not limited thereto. For example, the ratio of the position of each of the face parts to one of the length and width of the face or the ratio of the size of one of the face parts to the other may be used for comparison.

In addition, the relative relationship between the face parts (for example, the distance between face parts, the ratio of the position of each of the face parts to one of the length and width of the face, the ratio of the size of one of the face parts to the other) may be used for weighting purposes in the makeup part image determination process (for example, step S209 illustrated in FIG. 4). For example, suppose that as a result of comparison of the shape of a predetermined face part in the user face image with that in each of the adjusted face images (for example, the process described in FIGS. 5 and 9), the plurality of second difference values are the same. Then, the image determination unit 103 may select the makeup part image in the adjusted face image having the smaller second difference value regarding the relative relationship between the face parts.

Modification 3

In the above-described embodiment, the image determination unit 103 may compare the color information (for example, the hue, saturation, and brightness) regarding the hair, skin, lips, and the like extracted from the user face image with that extracted from each of the target face and the adjusted face. Thereafter, the image determination unit 103 may determine/change the color of a makeup part image representing a predetermined makeup item (for example, foundation, concealer, eyebrow, blush, or lipstick) to a color set for a face image having a difference value that is greater than or equal to the threshold value or the smallest difference value.

Modification 4

While the above embodiment has been described with reference to the makeup application assist device 100 that acquires an adjusted face image from the image pickup device 200, the processing is not limited thereto.

For example, to acquire an adjusted face image, the makeup application assist device 100 may select, from among the plurality of face images stored in the storage device 500, the one including a predetermined face part (for example, the outline) having a facial feature whose difference value from the facial feature of the face part in the target face image is the largest.

In addition, for example, the makeup application assist device 100 may receive an operation to set the difference value of the facial feature for each of the face parts. Thereafter, the makeup application assist device 100 may acquire the adjusted face image on the basis of the settings. For example, the makeup application assist device 100 receives the setting indicating that the second difference value with respect to the outline is less than or equal to the threshold value and the second difference with respect to each of the face parts (e.g., the eye, nose, and lip) is greater than the threshold value. In this case, the makeup application assist device 100 acquires, from among the plurality of face images stored in the storage device 500, the one that satisfies the set condition. The set condition can be determined in any way by the user of the makeup application assist device 100.

Modification 5

While, as illustrated in FIG. 6, the above embodiment has been described with reference to the case where an eyeshadow makeup part image is superimposed on the user face image in which the user opens both eyes and is displayed, the user face image is not limited thereto.

For example, in addition to the user face image in which the user opens both eyes, a user face image in which the user closes one eye may be captured. Thereafter, the eyeshadow makeup part image may be superimposed on the latter user face image (i.e., the image in which the user closes one eye) and may be displayed. The makeup part image presents the eyeshadow applied to the eyelid when the user closes the eye.

Note that as the eyeshadow makeup part image, either the eyeshadow makeup part image for the open eye or the makeup part image for the closed eye may be used. Alternatively, the eyeshadow makeup part image may be deformed on the basis of the face feature points so as to support both the open eye and the closed eye.

Modification 6

While, as illustrated in FIG. 6, the above embodiment has been described with reference to the makeup part images each being superimposed on the user face image and representing the shape and color of a makeup item as an example, the makeup part image may represent only the shape of the makeup item. An image representing only the shape of the makeup item is an image representing the periphery of the makeup item with, for example, a dotted line or a solid line.

Modification 7

While the above embodiment has been described with reference to, as an example, the makeup procedure information displayed in the screen as a still image, the user may be notified of predetermined details of the makeup procedure information by speech sound or a moving image.

Modification 8

The above embodiment has been described with reference to an example in which a makeup part image is adopted from an adjusted face image having the smallest second difference value in the makeup part image determining process illustrated in FIG. 4 (for example, step S209 illustrated in FIG. 4). If a plurality of second difference values are the smallest, information about the user (hereinafter referred to as "user related information") may be used for weighting, and one of the adjusted face images may be selected as the adjusted face image from which the makeup part image is to be adopted.

The user related information includes, for example, the user's preference of makeup (for example, the category of color of a makeup item and the tint of the color of the makeup item), the user's purchase history of makeup items (cosmetics), makeup items (cosmetics) currently held by the user and the like.

For example, if, in step S209 illustrated in FIG. 4, a plurality of second difference values are the smallest, the makeup application assist device 100 may select an adjusted face image that matches the user related information (for example, an adjusted face image having a similar category of color and a similar tint of the color). Thereafter, the makeup application assist device 100 may adopt the makeup part image in the selected adjusted face image.

Modification 9

In the above embodiment, a makeup salesperson at an in-store makeup counter, for example, may additionally make adjustments to the makeup part image determined in the makeup part image determination process by a manual operation. The examples of the adjustment include a change in the shape, color, or position of the determined certain makeup part image and addition of a makeup part image other than the determined makeup part image. The makeup application assist device 100 reflects the adjustments when generating makeup procedure information.

Note that the makeup application assist device 100 may store, in the storage device 500, information indicating the details of adjustment (hereinafter referred to as "adjustment information") for each of the users. For example, if the same adjustment (for example, a change in color of the eyeshadow makeup part image) is made for one user a plurality of times, the makeup application assist device 100 learns the adjustment tendency on the basis of a plurality of pieces of adjustment information. Thereafter, if a plurality of second difference values are the smallest in the next makeup part image determination process (step S209 illustrated in FIG. 4), the makeup application assist device 100 may select one of the adjusted face images that matches the learned tendency (for example, the adjusted face image having a similar color category and similar tint) and may adopt the makeup part image in the adjusted face image.

Modification 10

In the above-described embodiment, if one of the users uses the makeup application assist device 100 a plurality of times to generate a plurality of pieces of makeup procedure information for the user, the makeup application assist device 100 may instruct the storage device 500 to store a plurality of pieces of makeup procedure information for each of the users.

The makeup application assist device 100 learns the feature (for example, color category or color tint) of each of the makeup part images to be adopted on the basis of the plurality of pieces of makeup procedure information. Thereafter, if a plurality of second difference values are the smallest in the next makeup part image determination process (step S209 illustrated in FIG. 4), the makeup application assist device 100 may select one of the adjusted face images that matches the learned feature (for example, the adjusted face image having a similar color category and similar tint) and may adopt a makeup part image in the adjusted face image.

Modification 11

In the above embodiment, after the user actually applies makeup on the basis of the makeup procedure information, the user may input feedback information indicating the impression and the like to the terminal device 600 and transmit the feedback information to, for example, the storage device 500.

The feedback information includes, for example, information about a makeup item for which the makeup procedure information (e.g., the application technique information 74) is of some help and a makeup item and a product (the model number or product name) the user likes.

For example, if, in step S209 illustrated in FIG. 4, a plurality of second difference values are the smallest, the makeup application assist device 100 may select one of the adjusted face images that matches the feedback information (for example, the adjusted face image having a similar color category and similar tint) and may adopt the makeup part image in the adjusted face image.

Note that if a plurality of pieces of feedback information are stored in the storage device 500 for each of the users, the makeup application assist device 100 may learn the user's preference (for example, the category of color and the color tint of each of the makeup items) on the basis of the plurality of pieces of feedback information. Thereafter, in the next makeup part image determination process (step S209 illustrated in FIG. 4), if a plurality of second difference values are the smallest, the makeup application assist device 100 may select, from among the adjusted face images, the one that matches the learned user's preference (for example, the adjusted face image having a similar color category and similar tint) and may adopt the makeup part image in the adjusted face image.

At this time, to transmit the feedback information, the user may be allowed to post the feedback information to a social networking service (SNS). To facilitate posting of the feedback information by the user, the makeup procedure information illustrated in FIG. 6 may include link information to an SNS, such as Facebook, Twitter (registered trademark), Instagram, or Google Plus. When a user posts a message to the SNS, a hashtag may be automatically embedded in the posted message. In this manner, the users can collect the posted information and analyze the posted information to find a popular makeup design and a popular cosmetic product.

Modification 12

In addition to the information described above, the user related information described in Modification 8 may include, for example, the user's age, gender, nationality, place of residence, hometown, skin problems, ideal skin condition, and the past medical history (e.g., the name of a medical institution, the date and time of treatment, and a medical treatment part) provided by medical institutions (e.g., a dermatologist, an aesthetic dermatologist, or a cosmetic surgeon).

Such information is input from a predetermined device (for example, the makeup application assist device 100 or the terminal device 600) by, for example, an authorized person in, for example, a store or a medical institution or the user themselves. The user related information including the input information is sent from the predetermined device to the storage device 500 and is stored in the storage device 500 in association with the user identification information.

Thereafter, when, for example, generating the makeup procedure information, the makeup application assist device 100 may associate the user related information (for example, the nationality, age, and gender) with the generated makeup procedure information and outputs the information to a predetermined device (for example, a cosmetic development company or a sales store). Since these pieces of information are associated with each other, it can be determined what type of makeup is preferred by the users with what attribute. Consequently, the information can be used for, for example, development of cosmetics and advice and recommendation of products provided by a customer service representative in front of the customer.

Modification 13

The foregoing description of the embodiment has been given with reference to the case where the makeup application assist device 100 performs both the process of generating the template data set and the adjusted data set (the makeup part image table) and the process of generating the makeup procedure information as an example. The process of generating the template data set and the adjusted data set (the makeup part image table) may be performed by a device other than the makeup application assist device 100.

Modification 14

A subset of the constituent elements of the makeup application assist device 100 (the image acquisition unit 101, the image analysis unit 102, the image determination unit 103, and the information generation unit 104) may be physically separated from the other constituent elements. In this case, the separated constituent elements need to communicate with each other. For example, a subset of the functions of the makeup application assist device 100 may be provided by cloud computing.

Modification 15

In addition, the product information 75 described in the makeup procedure information illustrated in FIG. 6 may include link information to the selling Web site of each of the products. As a result, the user can select any product information from the makeup procedure information and display the selling Web site to purchase the product online. At this time, the user does not directly access the selling Web site by using the product information but accesses the selling Web site from the product information via the selling Web site access information acquisition site. The selling Web site access information acquisition site records the information indicating that the user has accessed the selling Web site by using the makeup procedure information. In this manner, access information to the selling Web site accessed by a plurality of users is recorded and accumulated. As a result, analysis can be made to know a product a particular user likes, a product a plurality of users like, and the trend in the market.

Modification 16

The makeup procedure information generated by the information generation unit 104 illustrated in FIG. 1 may be displayed by the terminal device 600 physically connected to the makeup application assist device 100 or another terminal device not physically connected to the makeup application assist device 100 (hereinafter referred to as a "display terminal"). Even when the display terminal is not physically connected to the makeup application assist device 100, the display terminal can be connected to a network by using a variety of wireless communication techniques. To display the makeup procedure information by a display terminal that is not physically connected to the makeup application assist device 100, the information generation unit 104 may upload the generated makeup procedure information to the cloud. Thereafter, the display terminal may access the makeup procedure information on the cloud, acquire the makeup procedure information, and display the makeup procedure information. In this case, to access the makeup procedure information, the display terminal may receive the URL of the makeup procedure information by e-mail, or the display terminal may read the QR code (registered trademark). Thus, the display terminal may acquire the link to the makeup procedure information.

Summary of Present Disclosure

According to the present disclosure, a makeup application assist device includes an image acquisition unit that acquires a user face image, a target face image in which a makeup item having predetermined shape and color is assigned to each of face parts, and an adjusted face image in which a feature of each on a subset of the face parts differs from a feature of the face part in the target face image and a makeup item having predetermined shape and color is assigned to each of the face parts, an image determination unit that adopts the makeup item assigned to a face part in the target face image if a difference value between a facial feature extracted from the user face image and a facial feature extracted from the target face image is less than or equal to a threshold value and adopts the makeup item assigned to each on the subset of the face parts in the adjusted face image and the makeup item assigned to each of the rest of the face parts in the target face image if the difference value is greater than the threshold value, and an information generation unit that generates makeup procedure information to be presented to a user, where the makeup procedure information includes a procedure for using the adopted makeup items.

Note that in the above-described makeup application assist device, the image determination unit determines whether a first difference value between the facial feature of a predetermined face part extracted from the user face image and the facial feature of the predetermined face part extracted from the target face image is less than or equal to the threshold value. If the first difference value is less than or equal to the threshold value, the image determination unit adopts the makeup item assigned to the predetermined face part in the target face image. If the first difference value is greater than the threshold value, the image determination unit determines whether a second difference value between the facial feature of the predetermined face part extracted from the user face image and the facial feature of the predetermined face part extracted from the adjusted face image is less than or equal to the threshold value. If the second difference value is less than or equal to the threshold value, the image determination unit adopts the makeup item assigned to the predetermined face part in the adjusted face image.

In addition, in the above-described makeup application assist device, the adjusted face image is provided in a plurality, and the image acquisition unit acquires the plurality of adjusted face images. The image determination unit determines whether the second difference value between the facial feature of the predetermined face part extracted from the user face image and the facial feature of the predetermined face part extracted from each of the adjusted face images is less than or equal to the threshold value. The image determination unit adopts the makeup item assigned in the adjusted face image having the smallest one of the second difference values each being less than or equal to the threshold value.

In addition, in the above-described makeup application assist device, the adjusted face image is provided in a plurality, and the image acquisition unit acquires the plurality of adjusted face images. The image determination unit determines whether the second difference value between the facial feature of the predetermined face part extracted from the user face image and the facial feature of the predetermined face part extracted from each of the adjusted face images is less than or equal to the threshold value. The image determination unit adopts, among the adjusted face images each having the second difference value less than or equal to the threshold value, the makeup item assigned in the adjusted face image having a weight assigned thereto in advance.

In addition, in the above-described makeup application assist device, the weight is set on a basis of information indicating one of an attribute of the user, a user's preference for makeup, and a relative relationship between predetermined face parts extracted from the user face image.

In addition, in the above-described makeup application assist device, the image determination unit generates a simulation image by superimposing an image of the adopted makeup item on the user face image and outputs the simulation image to a predetermined display device.

In addition, in the above-described makeup application assist device, the makeup procedure information includes at least information about a name of the adopted makeup item, information about a technique for using the adopted makeup item, and a simulation image obtained by superimposing an image of the adopted makeup item on the user face image.

In addition, in the above-described makeup application assist device, the image of the adopted makeup item is one of an image representing predetermined shape and color of the makeup item and an image representing only a predetermined shape of the makeup item.

According to the present disclosure, a makeup application assist method includes acquiring a user face image, a target face image in which a makeup item having predetermined shape and color is assigned to each of face parts, and an adjusted face image in which a feature of each on a subset of the face parts differs from a feature of the face part in the target face image and a makeup item having predetermined shape and color is assigned to each of the face parts, adopting the makeup item assigned to a face part in the target face image if a difference value between a facial feature extracted from the user face image and a facial feature extracted from the target face image is less than or equal to a threshold value and adopting the makeup item assigned to each on the subset of the face parts in the adjusted face image and the makeup item assigned to each of the rest of the face parts in the target face image if the difference value is greater than the threshold value, and generating makeup procedure information to be presented to a user, where the makeup procedure information includes a procedure for using the adopted makeup items.

The makeup supporting apparatus and the makeup supporting method according to the present disclosure are useful as a makeup supporting apparatus and a makeup supporting method for supporting user makeup.

What is claimed is:

1. A makeup application assist device comprising:
   image acquisition circuitry that acquires
      a user face image,
      a target face image in which a makeup item having predetermined shape and color is assigned to each of face parts of the target face image, and
      an adjusted face image in which a feature of each face part of a subset of the face parts of the adjusted face image differs from a corresponding feature of a corresponding face part of the target face image, and
   wherein a makeup item having predetermined shape and color is assigned to each of the face parts;
   image determination circuitry that
      adopts the makeup item assigned to a face part in the target face image if a difference value between a facial feature of the face part extracted from the user face image and a corresponding facial feature of the face part extracted from the target face image is less than or equal to a threshold value, and
      adopts the makeup item assigned to each face part of the subset of the face parts of the adjusted face image and adopts the makeup item assigned to each of the rest of the face parts in the target face image not corresponding to the face parts of the subset of face parts of the adjusted face image if the difference value is greater than the threshold value; and
   an information generation circuitry which, in operation, generates makeup procedure information to be presented to a user, the makeup procedure information including a procedure for using the adopted makeup item assigned to the face part in the target face image if the difference value is less than or equal to the threshold value, and including a procedure for using the adopted makeup items assigned to the adjusted face image and assigned to the target face image if the difference value is greater than the threshold value.

2. The makeup application assist device according to claim 1, wherein the image determination circuitry determines whether a first difference value between the facial feature of a predetermined face part extracted from the user face image and the facial feature of the predetermined face part extracted from the target face image is less than or equal to the threshold value,
   wherein if the first difference value is less than or equal to the threshold value, the image determination circuitry adopts the makeup item assigned to the predetermined face part in the target face image,
   wherein if the first difference value is greater than the threshold value, the image determination circuitry determines whether a second difference value between the facial feature of the predetermined face part extracted from the user face image and the facial feature of the predetermined face part extracted from the adjusted face image is less than or equal to the threshold value, and
   wherein if the second difference value is less than or equal to the threshold value, the image determination circuitry adopts the makeup item assigned to the predetermined face part in the adjusted face image.

3. The makeup application assist device according to claim 2, wherein the image acquisition circuitry acquires a plurality of the adjusted face images, and
   wherein the image determination circuitry determines whether the second difference value between the facial feature of the predetermined face part extracted from the user face image and the facial feature of the predetermined face part extracted from each of the adjusted face images is less than or equal to the threshold value, and
   wherein the image determination circuitry adopts the makeup item assigned to the adjusted face image having the smallest one of the second difference values, each being less than or equal to the threshold value.

4. The makeup application assist device according to claim 2, wherein the image acquisition circuitry acquires a plurality of the adjusted face images, and
   wherein the image determination circuitry determines whether the second difference value between the facial feature of the predetermined face part extracted from the user face image and the facial feature of the predetermined face part extracted from each of the adjusted face images is less than or equal to the threshold value, and
   wherein the image determination circuitry adopts among the adjusted face images, each having the second difference value less than or equal to the threshold value, the makeup item assigned to the adjusted face image having a weight assigned thereto in advance.

5. The makeup application assist device according to claim 4, wherein the weight is set on a basis of information indicating one of an attribute of the user, a user's preference for makeup, and a relative relationship between predetermined face parts extracted from the user face image.

6. The makeup application assist device according to claim 1, wherein the image determination circuitry generates a simulation image by superimposing an image of the adopted makeup item on the user face image and outputs the simulation image to a predetermined display device.

7. The makeup application assist device according to claim 1, wherein the makeup procedure information includes at least information about a name of the adopted makeup item, information about a technique for using the adopted makeup item, and a simulation image obtained by superimposing an image of the adopted makeup item on the user face image.

8. The makeup application assist device according to claim 7, wherein the image of the adopted makeup item is one of an image representing a predetermined shape and color of the makeup item and an image representing only the predetermined shape of the makeup item.

9. A makeup application assist method comprising:
   acquiring
      a user face image,
      a target face image in which a makeup item having predetermined shape and color is assigned to each of face parts of the target face image, and
      an adjusted face image in which a feature of each face part of a subset of the face parts of the adjusted face image differs from a corresponding feature of a corresponding face part of the target face image, and wherein a makeup item having predetermined shape and color is assigned to each of the face parts;

adopting the makeup item assigned to a face part in the target face image if a difference value between a facial feature extracted from the user face image and a corresponding facial feature of the face part extracted from the target face image is less than or equal to a threshold value;

adopting the makeup item assigned to each face part of the subset of the face parts of the adjusted face image and adopts the makeup item assigned to each of the rest of the face parts in the target face image not corresponding to the face parts of the subset of face parts of the adjusted face image if the difference value is greater than the threshold value; and generating makeup procedure information to be presented to a user, the makeup procedure information including a procedure for using the adopted makeup item assigned to the face part in the target face image if the difference value is less than or equal to the threshold value, and including a procedure for using the adopted makeup items assigned to the adjusted face image and assigned to the target face image if the difference value is greater than the threshold value.

* * * * *